(12) United States Patent
Levit

(10) Patent No.: US 11,116,768 B2
(45) Date of Patent: Sep. 14, 2021

(54) COMBINATION TREATMENT FOR THE REGENERATIVE THERAPY OF TYPE 1 DIABETES MELLITUS PATIENTS

(71) Applicant: LEVICURE LTD., Tel Aviv-Jaffa (IL)

(72) Inventor: Shmuel Boris Levit, Hadera (IL)

(73) Assignee: Levicure Ltd., Tel Aviv (IL)

( * ) Notice: Subject to any disclaimer, the term of this patent is extended or adjusted under 35 U.S.C. 154(b) by 0 days.

(21) Appl. No.: 16/119,430

(22) Filed: Aug. 31, 2018

(65) Prior Publication Data
US 2019/0240218 A1 Aug. 8, 2019

(30) Foreign Application Priority Data
Feb. 6, 2018 (RU) .......................... RU2018104548

(51) Int. Cl.
| | | |
|---|---|---|
| A61K 31/4985 | (2006.01) | |
| A61K 31/4439 | (2006.01) | |
| A61K 31/197 | (2006.01) | |
| A61P 3/10 | (2006.01) | |
| A61K 31/5513 | (2006.01) | |
| A61K 31/19 | (2006.01) | |
| A61K 31/403 | (2006.01) | |
| A61K 31/513 | (2006.01) | |

(52) U.S. Cl.
CPC .......... *A61K 31/4985* (2013.01); *A61K 31/19* (2013.01); *A61K 31/197* (2013.01); *A61K 31/403* (2013.01); *A61K 31/4439* (2013.01); *A61K 31/513* (2013.01); *A61K 31/5513* (2013.01); *A61P 3/10* (2018.01)

(58) Field of Classification Search
CPC combination set(s) only.
See application file for complete search history.

(56) References Cited

U.S. PATENT DOCUMENTS

| | | | |
|---|---|---|---|
| 4,786,505 A | 11/1988 | Lovgren et al. | |
| 5,698,155 A | 12/1997 | Grosswald et al. | |
| 9,463,174 B2 * | 10/2016 | Wang | A61K 31/197 |
| 2014/0322213 A1 | 10/2014 | Wang et al. | |

FOREIGN PATENT DOCUMENTS

| | | | |
|---|---|---|---|
| EP | 2201952 A1 * | 6/2010 | ........... A61K 9/0007 |
| EP | 2201952 A1 | 6/2010 | |
| RU | 2440143 C2 | 11/2009 | |
| RU | 2601622 C1 | 11/2016 | |
| WO | 2006000567 A2 | 1/2006 | |

OTHER PUBLICATIONS

Suarez-Pinzon et al. Combination Therapy With a Dipeptidyl Peptidase-4 Inhibitor and a Proton Pump Inhibitor Induces Beta-Cell Neogenesis From Adult Human Pancreatic Duct Cells Implanted in Immunodeficient Mice Cell Transplantation, vol. 20, pp. 1343-1349, 2011 (Year: 2011).*

Ellis et al, Effect of sitagliptin on glucose control in adult patients with Type 1 diabetes: a pilot, double-blind, randomized, crossover trial, Diabet. Med. 28, 1176-1181 (2011).

Griffin et al., Combination therapy with sitagliptin and lansoprazole in patients with recent-onset type 1 diabetes (Repair-T1D): 12-month results of a multicentre, randomised, placebo-controlled, phase 2 trial, Lancet Diabetes Endocrinol 2014; 2: 710-18.

Takebayashi et al., Effect of proton pump inhibitors on glycemic control in patients with diabetes, World J Diabetes Aug. 25, 2015; 6(10): 1122-1131.

Osipenko et al., Issues of safety of proton pump inhibitors, Lechashchij Vrach, Aug. 31, 2016 https://www.lvrach.ru/2016/08/15436529/.

* cited by examiner

*Primary Examiner* — Kortney L. Klinkel
*Assistant Examiner* — William Y Lee
(74) *Attorney, Agent, or Firm* — Pearl Cohen Zedek Latzer Baratz LLP

(57) ABSTRACT

This invention applies to the field of medicine, namely to endocrinology, and intended for the treatment of type 1 diabetes mellitus.

The invention proposes a combination, containing a Dipeptidyl peptidase-4 (DPP-4) inhibitors, a proton pump inhibitors (PPI), and gamma-aminobutyric acid or a gamma-aminobutyric acid receptor agonists. This unique combination of medications and specific dosage of drugs leads to the regeneration (recovery) of the β-cells of the pancreas, which is presented by a dramatic reduction of insulin requirements up to a total insulin discontinuation in some persons.

2 Claims, 5 Drawing Sheets

COMBINATION TREATMENT FOR THE REGENERATIVE THERAPY OF TYPE 1 DIABETES MELLITUS PATIENTS

FIELD OF THE INVENTION

This invention relates to the field of medicine, namely, to endocrinology, and can be used to treat type 1 diabetes.

BACKGROUND ART

Diabetes mellitus type 1 (DM1, insulin-dependent diabetes, juvenile diabetes) is an autoimmune disease of the endocrine pancreas. Its main diagnostic sign is chronic hyperglycemia (high blood sugar), polyuria (frequent urination), and other signs and symptoms as: thirst, weight loss, excessive or decreased appetite; severe general fatigue. Additionally, a prolonged manifestation of the disease in the absence of diagnosis can lead to the poisoning of the body by some by-products of lipolysis (fat decomposition)—often expressed as ketone bodies production and specific odour coming from the skin and the mouth.

Until 1921, when insulin treatment was applied for the first time, this disease was regarded as fatal. Patients died from malnutrition and coma resulting from ketoacidosis (blood acidification due to production of acetone).

At the cornerstone of the pathogenetic mechanism of type 1 diabetes development is the insufficient production of insulin by endocrine cells (β-cells of the islets of Langerhans in the pancreas). Type 1 diabetes comprises 5%-40% of all diabetes cases, it is more likely to appear in childhood or adolescence and can be hereditary. Out of about 400,000,000 diabetic patients living in the world today, up to 40,000,000 are DM1 patients.

This type of diabetes is characterized by an early manifestation of symptoms that progress quickly over time.

Due to insulin deficiency, insulin-dependent tissues (liver, fat, and muscle) lose their ability to absorb blood glucose and, as a result, blood glucose level increases (hyperglycemia)—thus being the main diagnostic sign of diabetes mellitus. Insulin deficiency in adipose tissue causes lipolysis (fat breakdown), leading to an increased concentration of Free Fatty Acids (FFA) in the blood, while in the muscle tissue it leads to the disintegration of proteins, which creates an increased levels of amino acids in the bloodstream. Substrates from the catabolism of fats and proteins are transformed into ketone bodies by the liver; these ketones are then used by insulin-independent tissues (mainly the brain) to maintain an energy balance against the backdrop of insulin deficiency.

The exact cause of the disease is unknown. All over the world, it is considered to be an utterly incurable, disabling disease.

There are six stages of development of type 1 diabetes mellitus (DM1):

Genetic predisposition to diabetes, associated with the HLA system.

Hypothetical starting point: β-cells damage by various diabetogenic factors and by the stimulation of immune processes. Patients already have antibodies against the islet cells in a small titer, but insulin secretion does not yet appear to be compromised.

Active autoimmune insulitis—inflammation of the endocrine part of the pancreas. The antibody titer is high, the number of β-cells decreases, with the secretion of insulin decreasing as well.

Decreased insulin secretion. In stressful situations, it is possible to identify impaired glucose tolerance (IGT) in the patient, as well as impaired fasting glucose (IFG).

Clinical manifestation of diabetes, including a possible episode of the "honeymoon phase." The secretion of insulin is sharply reduced since more than 90% of β-cells have died or functionally paralyzed.

Complete destruction of β-cells, total cessation of insulin secretion.

Treatment of type 1 diabetes involves lifelong injections of insulin. Without this treatment, the disease progresses rapidly and leads to severe complications such as diabetic retinopathy, polyneuropathy, diabetic foot ulcers, ketoacidosis, and diabetic coma, diabetic cardiomyopathy, kidney failure, etc., all of which may lead to disability or result in the patient's death.

However, a constant intake of insulin can often lead to an overdose, which can give rise to several complications. The risk of hypoglycemia, which contributes to the development of brain damage, dementia, cardiovascular complications, atherosclerosis and arterial hypertension, is particularly high. Therefore, modern methods of treating type 1 diabetes are aimed at finding new drugs that can save the patient from the daily administration of insulin by preserving the β-cells and even regenerating the β-cell-pool.

Decapeptil Peptidase Inhibitors (DPP4i)

They can be selected, for example, from Sitagliptin, Linagliptin, Saxagliptin, Vildagliptin and others.

The drug Sitagliptin(Januvia) has been registered in many countries in the world. Sitagliptin may serve as a classic representative of a family of DPP4i. Sitagliptin increases the concentration of two known hormones of the incretin family: glucagon-like peptide 1 (GLP-1) and glucose-dependent insulinotropic peptide (GIP). Hormones of the family of incretins are secreted in the intestine during the day, with levels rising in response to food intake. Incretins are part of the internal physiological system of regulation of glucose homeostasis. At normal or elevated blood glucose levels, the hormones of the incretin family promote an increase in insulin synthesis, as well as its secretion by beta cells of the pancreas, due to the intracellular signaling mechanisms associated with cyclic AMP. A double-blind, randomized, cross-over, 8-week, preliminary study in adult patients with type 1 diabetes showed that the drug had significantly reduced blood glucose levels despite a reduction of total and lunch dose of insulin (Diabet Med. 2011 October; 28 (10): 1176-81 Effect of Sitagliptin on glucose control in an adult patient with Type 1 diabetes: a pilot, double-blind, randomized, crossover trial Ellis S L, Moser E G, Snell-Bergeon J K, Rodionova A S, Hazenfield R M, Garg S K.). This drug is now being considered for introduction into the clinical practice of type 1 diabetes treatment.

In addition, attempts have been made to create combined medications based on Sitagliptin and other DPP-4 inhibitors for the treatment of diabetes.

In particular, in an article by Griffin K J, Thompson P A, Gottschalk M, Kyllo J H, Rabinovitch A. Combination therapy with Sitagliptin and lansoprazole in patients with recent-onset type 1 diabetes (REPAIR-T1D): 12-month results of a multicentre, randomized, placebo-controlled, phase 2 trial. //Lancet Diabetes Endocrinol. 2014 September; 2 (9): 710-8, it is postulated that Sitagliptin and lansoprazole will maintain the beta-cell function in patients with type 1 diabetes. However, in the analysis, it was noted that not all participants were able to increase their glucagon-like peptide 1 and gastrin concentrations.

International application WO2006000567 discloses the use of a GLP-1 receptor agonist and/or a DPP-4 inhibitor and a proton pump inhibitor such as omeprazole or esomeprazole, in the manufacture of a medicament for the treatment of type 1 diabetes. However, this combination does not provide a significant reduction of the insulin dose.

GABA (Gamma-Amino Butyric Acid)

There is known gamma-aminobutyric acid (GABA), as well as other gamma-aminobutyric acid receptor agonists, like most anti-epileptic medications, Gamma-Pantene acid and even medical (legal) forms of Marijuana.

Recently GABA has been shown to provide the regeneration of β-cells in mouse and human cell cultures.

The U.S. Pat. No. 9,463,174 discloses a method for treating type 1 diabetes (T1D), including administering a therapeutically effective amount of gamma-aminobutyric acid (GABA) and an effective amount of a DPP-4 inhibitor, for example, Sitagliptin, to a T1D patient. GABA and the DPP-4 inhibitor are used in a single-dosage form or separate-dosage forms. The dosage includes GABA in 0.002 to 2 mg/kg of body weight. This combination does not lead to a significant recovery of beta cells of the pancreas.

PPI (Proton Pump Inhibitors)

There are known the proton pump inhibitors (U.S. Pat. No. 4,786,505, EP2201952). The proton pump inhibitor is administered orally at a daily dose of 10 to 40 mg, depending on the body weight. Proton pump inhibitors can be selected, for example, from omeprazole, pantoprazole, lansoprazole, rabeprazole, and esomeprazole.

Disclosure of the Invention

The goal of this invention is to provide a combination of substances that leads to a long-lasting anti-hyperglycemic effect, is safe, and has a favourable side effects profile.

This objective is achieved by using a unique combination consisting of a DPP-4, a proton pump inhibitor (PPI) and GABA (gamma-aminobutyric acid) or GABA-receptor agonist. This exclusive combination leads to a regeneration (recovery) of the β-cells of the pancreas and is intended for the treatment of type 1 diabetes.

Figure 1:
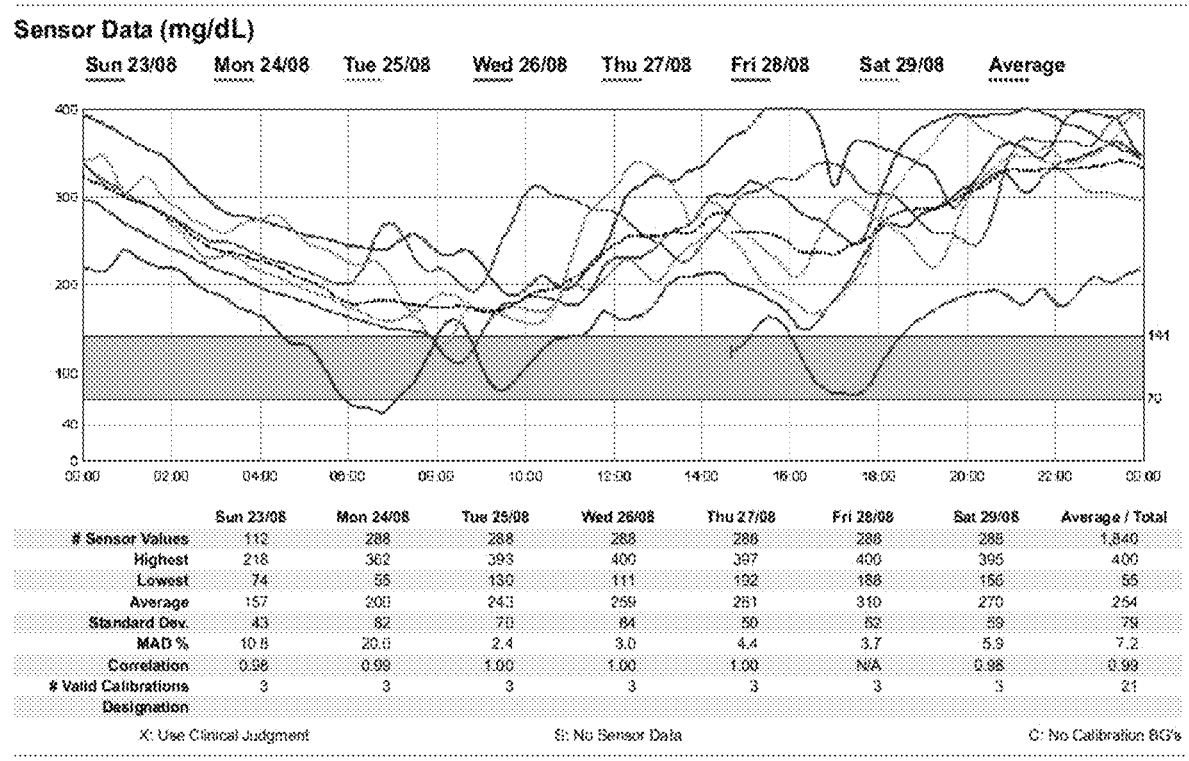
FIG. 1—shows graph of continuous glucose monitoring (CGM) data of the patient in Example 1, before starting triple therapy.

The administration of the three-drug combination according to the present invention is proposed for the treatment of Type 1 Diabetes (T1DM). More particularly, according to the present invention the inventors propose a combination of substances for use in regenerative therapy in patients with type 1 diabetes mellitus.

The first drug of the proposed combination belongs to the group of DPP-4 inhibitors (DPP4i). The DPP-4 inhibitor is administered orally at a daily dose of 25 to 100 mg, depending on the body weight. Examples of drugs of this group, which are suitable to be used in this invention, are DPP-4 inhibitors: alogliptin, linagliptin, saxagliptin, sitagliptin, and vildagliptin. The use of sitagliptin (Sitagliptin) in particular is preferable in the practice of this invention. These can be, for example, pills of sitagliptin manufactured by various companies.

The second drug of the proposed combination belongs to the PPI group. The proton pump inhibitor is administered orally at a daily dose of 10 to 40 mg, depending on the body weight. Proton pump inhibitors can be selected, for example, from omeprazole, pantoprazole, lansoprazole, rabeprazole, and esomeprazole. Omeprazole is preferred in the practice of this invention, for example in the form of pills or capsules.

The third drug of the proposed combination is gamma-aminobutyric acid (GABA), as well as other gamma-aminobutyric acid receptor agonists. The drug is given in a daily dose of 125 to 500 mg three times a day, depending on the body weight. Capsules of GABA, gelatine or cellulose (U.S. Pat. No. 5,698,155) or tablets (Aminalon) can be used. GABA agonists, such as baclofen, phenibut, pantogam, and anti-epileptic medications such as Valproic acid, Depalept, Topamax, Carbamazepine, and medical cannabis, can also be used instead of GABA.

Oral forms include any pharmaceutically acceptable dosage forms, powders, granules, capsules, tablets, microcapsule suspensions, and the like. The medications can be used alone or in a single dosage form, for example in the form of capsules.

The technical result of the invention lies in the fact that the administration of the drugs in this combination allows for a significant reduction in the need for insulin, and in some cases, it is even possible to stop insulin injections completely.

Drugs of the DPP-4i group (e.g., Sitagliptin, Vildagliptin, Saxagliptin, etc.) help in the regeneration of β-cells. This is due in particular to the fact that medications of the DPP-4i family are capable of modulating the immune response by limiting autoimmune activity, reducing the inflammatory component (insulitis) and ultimately achieving the regeneration of the β cells of the pancreas.

DPP-4 inhibitors (DPP-4i) block the activity of the DPP-4 enzyme, which leads to an increase in both concentration and the duration of action of GLP-1 and GIP. They are taken orally and provide a healthy physiological level of incretins in the blood.

A critically important feature of the effect of GLP-1 on the function of p and a cells is its glucose-dependent nature. This means that the GLP-1 stimulates insulin secretion and, on the other hand, suppresses the production of glucagon only under conditions of hyperglycemia. Once plasma glucose drops to a regular level, the effects above of GLP-1 subside, making it a reliable physiological mechanism for preventing the development of a hypoglycemic state.

GABA (Gamma Amino Butyric Acid) affects both β and α-cells, their functions and the viability of the pancreas as a whole. This substance is widely used as a food supplement. In α-cells, GABA induces hyperpolarisation of the membrane and suppresses glucagon, whereas in β-cells it induces membrane depolarization and increases insulin secretion. Also, GABA has a multi-directional positive effect on β-cells, which includes the stimulation of cell proliferation and anti-apoptosis, thus making it an attractive option for complex treatment of diabetes.

Proton pump inhibitors inhibit Na+/K+-ATPase (proton pump) on the apical membrane of parietal cells of the gastric mucosa and ensure the achievement of clinical, endoscopic remission in all acid-dependent diseases, including those requiring prolonged or continuous therapy. For an extended period during the day, they maintain pH values in the stomach within limits favorable for the healing of stomach or duodenal ulcers. The general effect of the pharmacological action of the drugs of this group is the increase of Gastrin in the blood and the pancreatic tissue. Gastrin is a natural stimulant for the recovery (regeneration) of pancreatic cells.

In the light of the above, the use of triple therapy (DPP-4i+GABA+PPi) appears to be promising for maintaining pancreatic function and for controlling type 1 diabetes in human patients.

The above-mentioned triple combination showed unexpectedly good results. The possibility of carrying out the invention can be illustrated by the following examples presented below.

EXAMPLE 1

An 82-year-old patient, with 35 years of type 1 diabetes. For the last ten years, has been taking 30 units of Insulin Lantus (Glargine) per day, and 10 units of Apidra (Glulisin) daily with each meal. Glucophage 850 mg/day. Anamnesis: diabetes retinopathy, BMI=27, frequent night hypoglycemia, hypothyroidism, HBa1C=10.5%; A/GAD (antibodies against glutamate decarboxylase)=3.8 (nearly a fourfold increase); Undetectable C-peptide.

Figure 2:
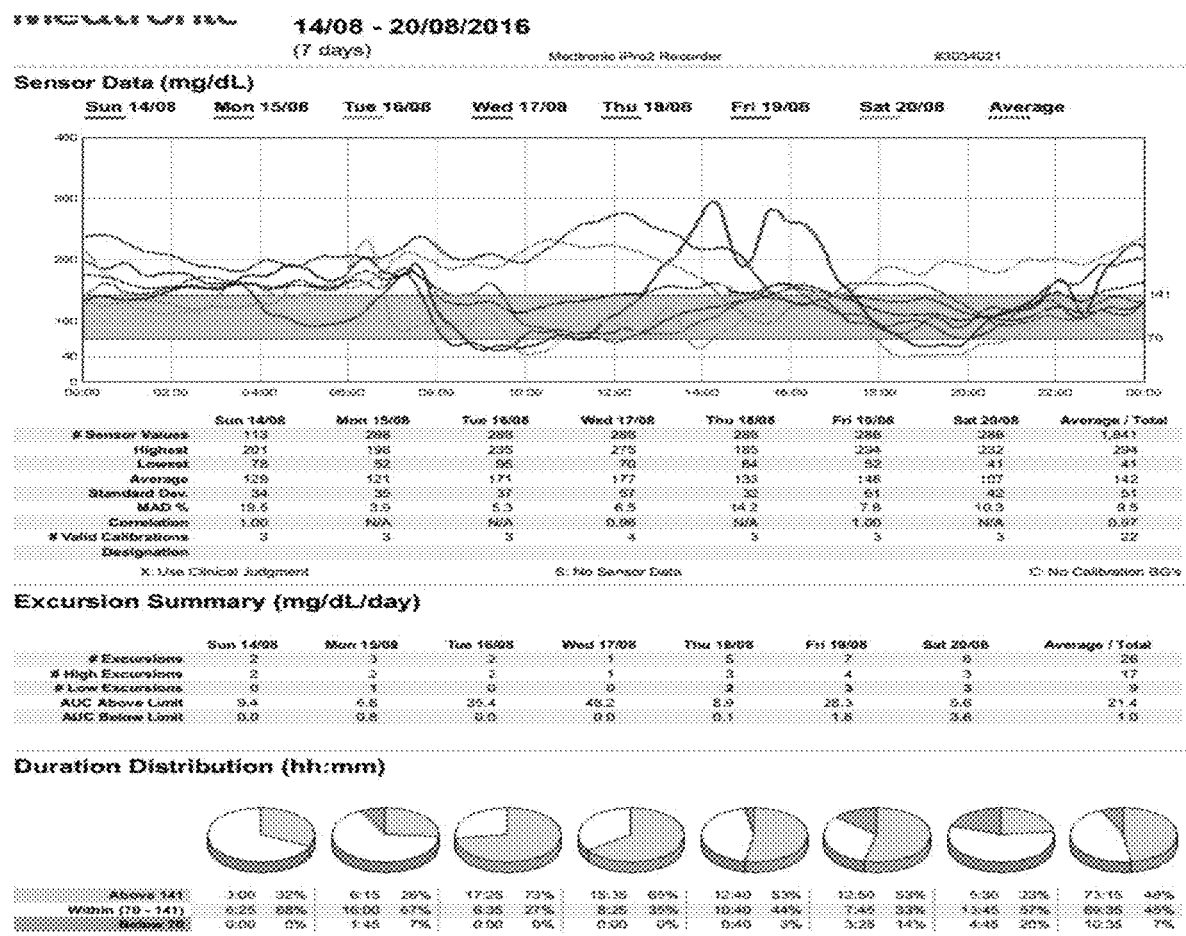
FIG. 2—shows graph of continuous glucose monitoring (CGM) data during the triple therapy, accompanied by dramatic insulin requirement reduction, of the patient in Example 1; in April, 2018 his C-peptide became detectable.

The results of the CGM (Continuous Glucose Monitoring) study before triple therapy are shown in FIG. 1. The patient was prescribed with an orally-administered combination in accordance with the invention. FIG. 2 shows the changes during the treatment. The patient's need for insulin is reduced to 24.3 units a day. 7% of the time, the patient is in a hypoglycemic state(blood sugar below 70 mg/dL), glycated hemoglobin-HBa1C=6.6%.

EXAMPLE 2

Figure 3:
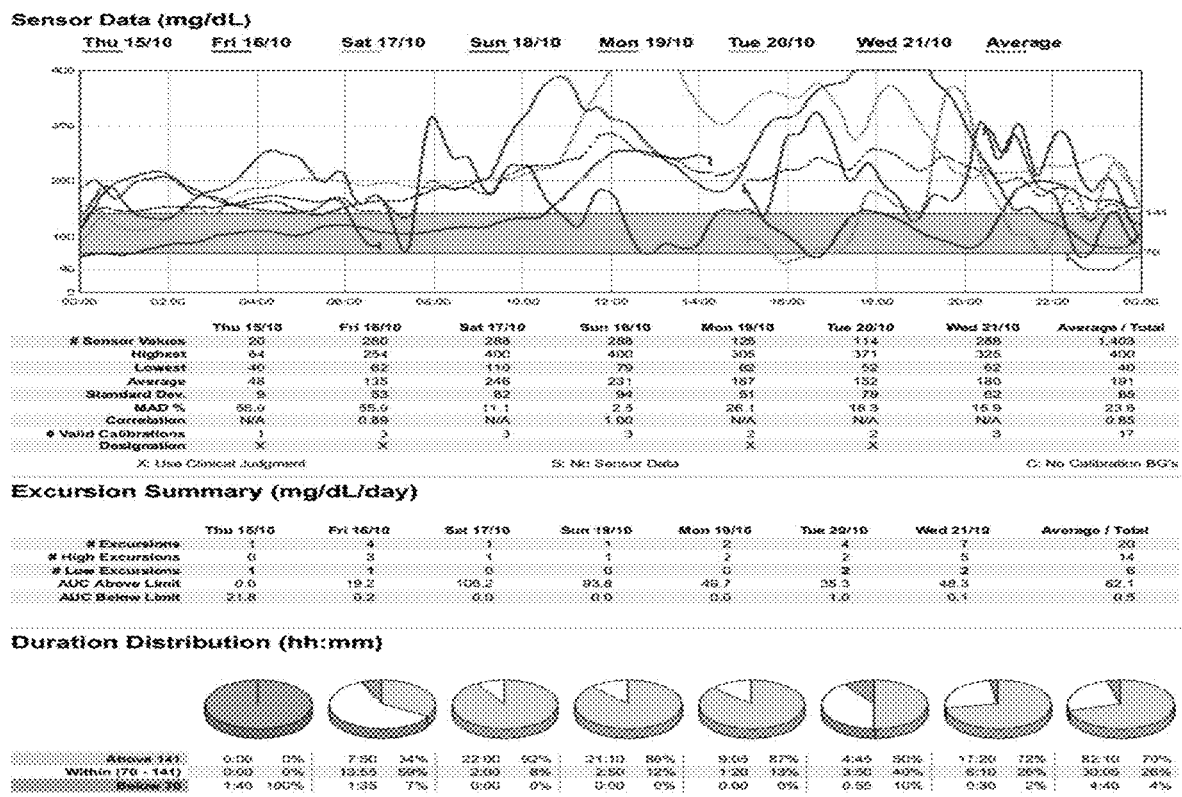
FIG. 3—CGM data of the patient in Example 2, before starting treatment.

19.5-year-old patient, diagnosed with type 1 diabetes since September 2015. Prior to his admission to the clinic, he has been treated with insulin Lantus (Glargine) 26 units in the morning, and with insulin Actrapid (Glulisine) three times a day during meals: 16-14-12 units. Analysis: unremarkable anamnesis, ketoacidosis, HBa1C=12.8%. The results of the CGM study are shown in FIG. 3.

Figure 4:
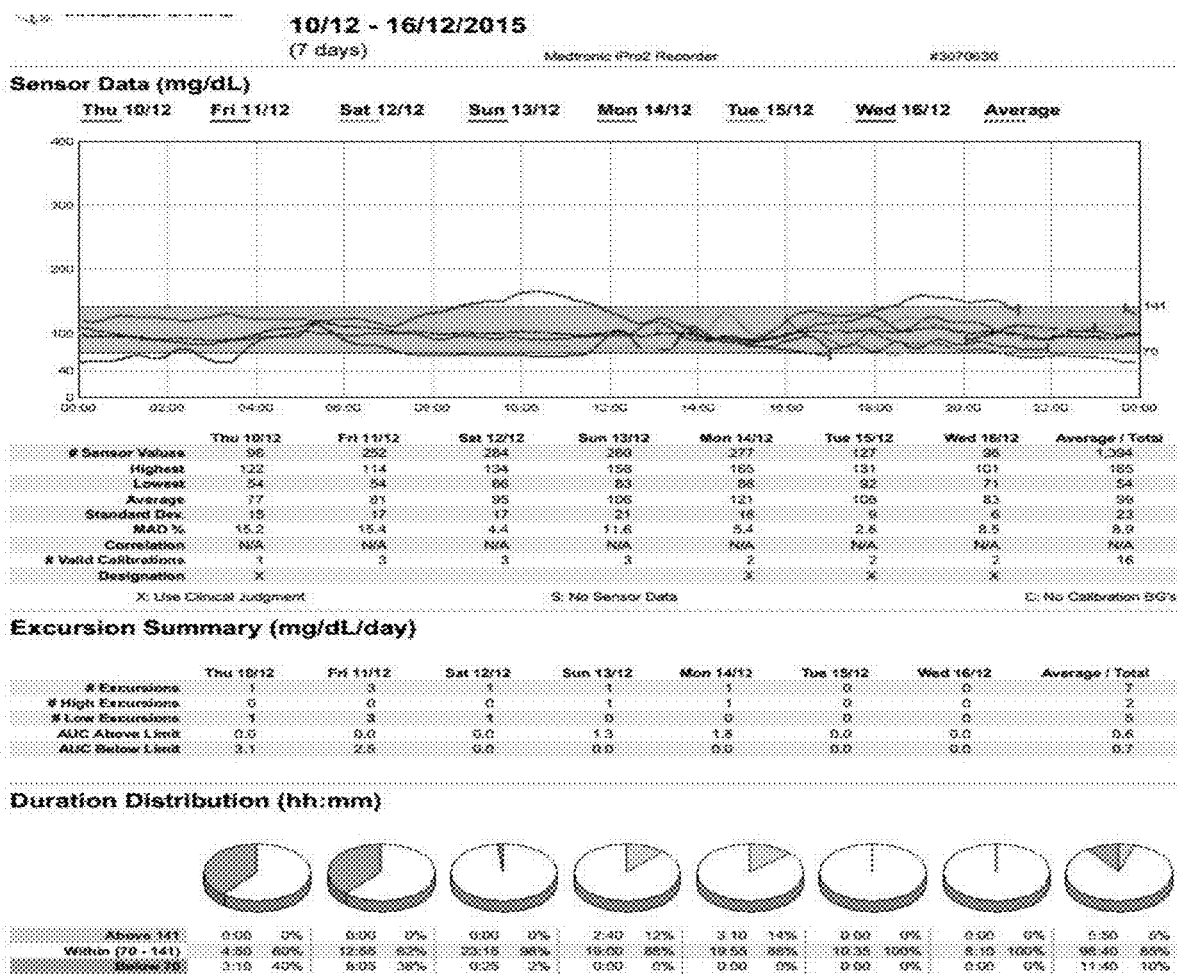
FIG. 4—CGM data of the patient in Example 2, two months on triple therapy and total Insulin discontinuation FIG. 5—CGM data of the patient in Example 2, eight months on the triple therapy and total Insulin discontinuation.
Figure 5:
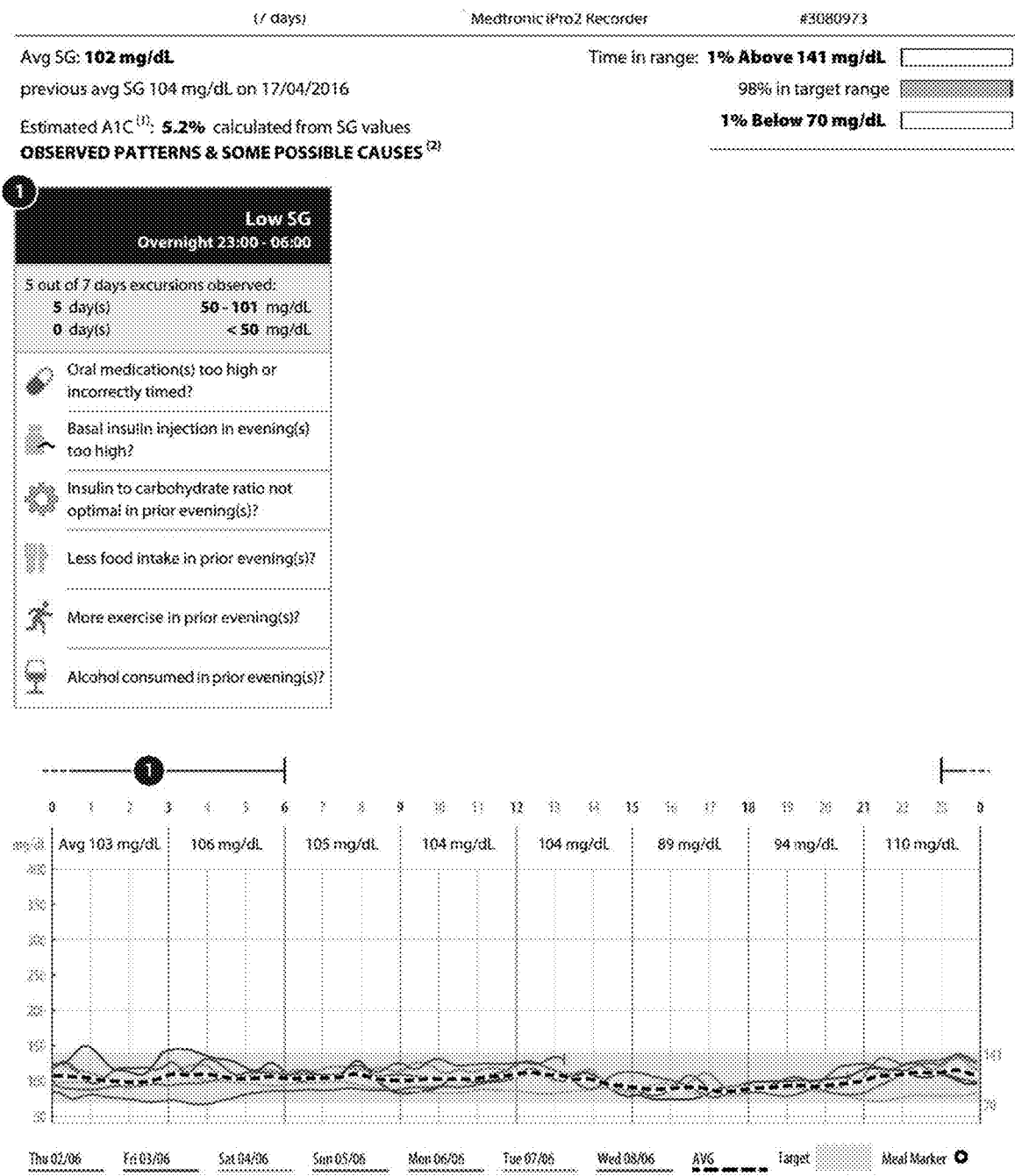

The patient was prescribed with an orally-administered combination in accordance with the invention. The combination included sitagliptin at 50 mg per day, pantoprazole at 10 mg per day, and GABA at 300 mg three times a day. FIG. 4 and FIG. 5 demonstrate an absence of the need for insulin. HBa1C=5.1%. The patient did not require any insulin for almost 1.5 years. Now he is well—controlled on 20-22 units of basal insulin only.

A total of 46 people took part in the research More than 50% of the patients were able to significantly reduce their insulin doses, with five patients stopping insulin injections completely for long-term period (months and even years). Also, the data demonstrate that the pancreas has regenerated its function. Patients in this category can be very different. In particular, as can be seen from Example 1, even severe forms of diabetes in patients of advanced age are responsive to treatment. The combination can be used even in children.

These studies conducted in humans demonstrate not only surprisingly good results but also the unexpectedly low toxicity of this therapy, with virtually no side effects.

Thus, significant results have indeed been obtained. That is, not only does this invention lead to a substantial decrease in the need for insulin injections—which in itself is outstanding and proves the restoration and regeneration of pancreatic function—but it also allows for the possibility of a complete long-term insulin discontinuation, although it is universally believed that Type 1 diabetes (T1D) is an irreversible disease.

The invention claimed is:

1. A method of using an orally-administered combination of compounds in regenerative therapy in patients with type 1 diabetes mellitus, comprising:
   daily administering orally between 25 and 100 mg of dipeptidyl peptidase (DPP-4) inhibitors comprising a therapeutically effective amount of DPP-4 inhibitors;
   daily administering orally between 10 and 40 mg of proton pump inhibitor (PPI) comprising a therapeutically effective amount of PPI; and
   thrice daily administering orally between 125 and 500 mg of a gamma-aminobutyric acid preparation (GABA) or GABA receptor agonist, comprising a therapeutically effective amount of GABA or a GABA receptor agonist.

2. The method of claim 1,
   wherein the DPP-4 inhibitor is sitagliptin, and
   wherein the PPI is omeprazole.

* * * * *